US006783511B2

(12) United States Patent
Komtebedde et al.

(10) Patent No.: US 6,783,511 B2
(45) Date of Patent: Aug. 31, 2004

(54) METHODS AND DEVICES FOR OCCLUDING A PATIENT'S ASCENDING AORTA AND DELIVERING OXYGENATED BLOOD TO THE PATIENT

(75) Inventors: Jan Komtebedde, Cupertino, CA (US); Ronald R. Hundertmark, San Mateo, CA (US); John Soo Hoo, Union City, CA (US); Gerardo Rosales, Redwood City, CA (US); Lawrence C. Siegel, Hillsborough, CA (US); Mark A. Groh, Ashville, NC (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/835,286

(22) Filed: Apr. 12, 2001

(65) Prior Publication Data
US 2002/0151869 A1 Oct. 17, 2002

(51) Int. Cl.[7] .................. A61M 29/00; A61M 37/00; A61M 3/00
(52) U.S. Cl. ................ 604/102.01; 604/43; 604/6.16
(58) Field of Search ............... 604/4.01, 6.16, 604/43, 97.01, 102.01, 103.07, 171, 173, 912, 915, 916, 96.01, 27, 164.09

(56) References Cited

U.S. PATENT DOCUMENTS

| | | | |
|---|---|---|---|
| 5,270,005 A | 12/1993 | Raible | |
| 5,275,622 A | 1/1994 | Lazarus et al. | |
| 5,314,418 A | 5/1994 | Takano et al. | |
| 5,322,500 A | 6/1994 | Johnson et al. | |
| 5,322,509 A | 6/1994 | Rickerd | |
| 5,324,260 A | 6/1994 | O'Neil et al. | |
| 5,332,402 A | 7/1994 | Teitelbaum | |
| 5,370,618 A | 12/1994 | Leonhardt | |
| 5,374,245 A | 12/1994 | Mahurkar | |
| 5,380,282 A | 1/1995 | Burns | |
| 5,382,239 A | 1/1995 | Orr et al. | |
| 5,395,331 A | 3/1995 | O'Neil et al. | |
| 5,397,306 A | 3/1995 | Nobuyoshi et al. | |
| 5,397,351 A | 3/1995 | Pavcnik et al. | |
| 5,411,027 A | 5/1995 | Wiklund et al. | |
| 5,411,552 A | 5/1995 | Andersen et al. | |
| 5,433,700 A | * 7/1995 | Peters | 604/113 |
| 5,439,443 A | 8/1995 | Miyata et al. | |
| 5,480,424 A | 1/1996 | Cox | |

(List continued on next page.)

FOREIGN PATENT DOCUMENTS

| | | |
|---|---|---|
| EP | 1 025 876 A | 8/2000 |
| EP | 1 060 758 A | 12/2000 |
| WO | WO 99 37202 A | 7/1999 |

OTHER PUBLICATIONS

Visser, Susan A., Hergenrother, Robert W., and Cooper, Stuart L. (1996). Polymers. in Biomaterials Science: An Introduction to Materials in Medicine, B.D. Ratner et al., eds. Academic Press, San Diego, pp 50–60.*

Nellessen T, et al.; "Cannula with proximal and distal end has mesh outlets at distal end, and lumen between ends"; English Abstract of EP 1025876; Aug. 09, 2000; Dialog File No. 351 Accession No. 13344118; Derwent World Patents Index; 2004 Derwent Information Ltd.

European Search Report EP02252590 dated Jan. 26, 2004.

Primary Examiner—Brian L. Casler
Assistant Examiner—Mark K. Han (57) ABSTRACT

A device for delivering oxygenated blood and occluding the ascending aorta is provided. The device has a blood flow lumen with a movable portion. The movable portion is movable from a position contained within a body of the device to a position which extends outwardly from the device. The movable portion is made of a tube of flexible material and everts when moving to the extended position.

25 Claims, 7 Drawing Sheets

U.S. PATENT DOCUMENTS

| | | |
|---|---|---|
| 5,525,388 A | 6/1996 | Wand et al. |
| 5,527,292 A | 6/1996 | Adams et al. |
| 5,533,957 A | 7/1996 | Aldea |
| 5,562,606 A | 10/1996 | Huybregts |
| 5,578,010 A | 11/1996 | Ashby |
| 5,928,192 A * | 7/1999 | Maahs .................... 604/96.01 |
| 6,086,557 A | 7/2000 | Morejohn et al. |
| 6,090,096 A | 7/2000 | St. Goar et al. |
| 6,090,097 A | 7/2000 | Pastrone |
| 6,176,851 B1 | 1/2001 | Tsugita et al. |
| 6,210,365 B1 * | 4/2001 | Afzal ......................... 600/435 |
| 6,217,548 B1 * | 4/2001 | Tsugita et al. ............. 604/509 |
| 6,350,252 B2 * | 2/2002 | Ray et al. .................. 604/105 |

\* cited by examiner

METHODS AND DEVICES FOR OCCLUDING A PATIENT'S ASCENDING AORTA AND DELIVERING OXYGENATED BLOOD TO THE PATIENT

BACKGROUND OF THE INVENTION

The present invention relates to devices and methods for occluding a patient's ascending aorta and delivering oxygenated blood to the patient. In particular, the present invention is useful for placing and maintaining a patient on bypass support.

SUMMARY OF THE INVENTION

The present invention provides a device for occluding a patient's ascending aorta and delivering oxygenated blood to the patient. The device includes a blood flow lumen having a movable portion. The movable portion moves from a position contained within a body of the device to a position which extends outwardly from the body. The movable portion preferably everts when moving to the extended position to form the distal portion of the blood flow lumen. The device preferably has an expandable member, such as a balloon, to occlude the ascending aorta. The device may also have an additional lumen for delivering cardioplegic fluid or for venting the ascending aorta.

The movable portion is preferably everted by the flow of oxygenated blood through the blood flow lumen. The movable portion is preferably a flexible tube made of a suitable material such as polyurethane or expanded PTFE. The movable portion provides a soft, atraumatic blood delivery lumen. In a preferred embodiment, the movable portion extends downstream beyond the neck and head vessels so that blood is directed down the descending aorta.

The movable portion may also be manually movable to the extended position. When the movable portion is manually movable, the movable portion is preferably a separate lumen which slidingly engages the body.

The present invention is also directed to a method of occluding a patient's ascending aorta and delivering oxygenated blood to the patient. A device having a body, an expandable member and a blood flow lumen is introduced into the patient's ascending or transverse aorta so that the expandable member is positioned in the ascending aorta. The movable portion is contained within the body during introduction of the device. After introduction, the movable portion is extended outwardly from the body. The movable portion preferably everts to the extended position when oxygenated blood is delivered. Of course, the movable portion may be extended in any other manner. For example, the movable portion may be a manually movable lumen or could be a lumen which is floated into position without everting.

These and other aspects and advantages of the invention will become apparent from the following description, claims and drawings.

DESCRIPTION OF THE PREFERRED EMBODIMENTS

Figure 1:
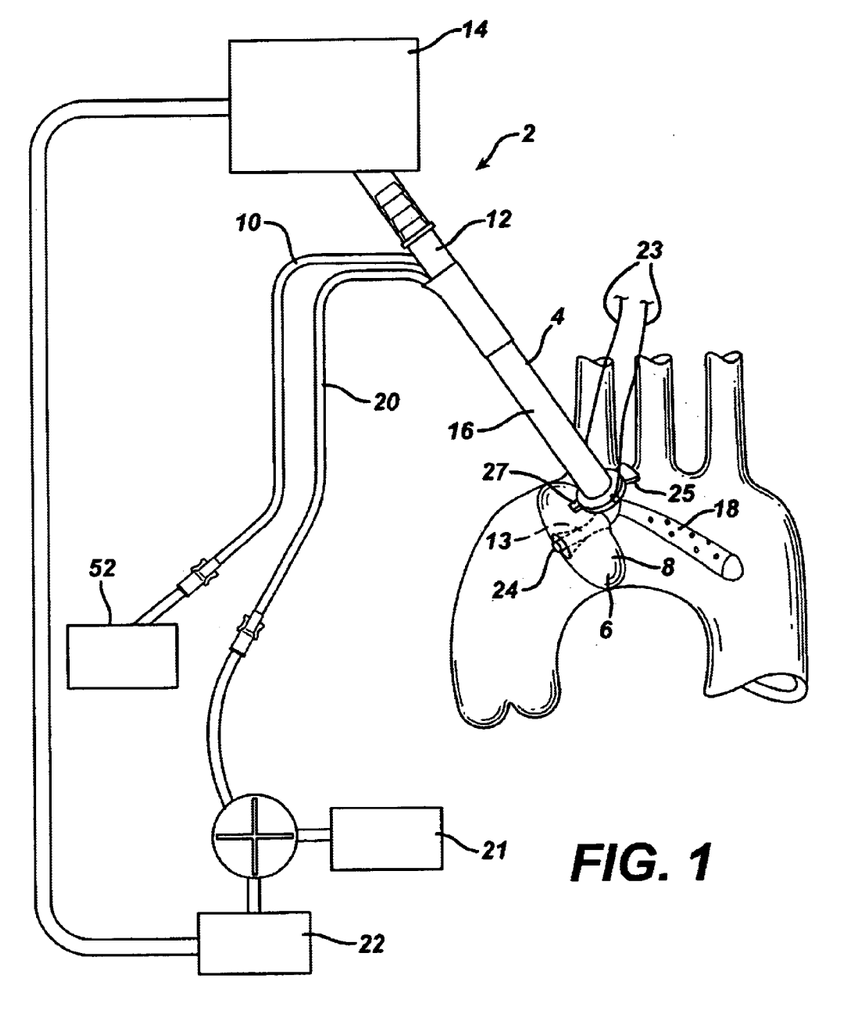
FIG. 1 shows a device for occluding a patient's ascending aorta and delivering oxygenated blood to the patient.
Figure 2:
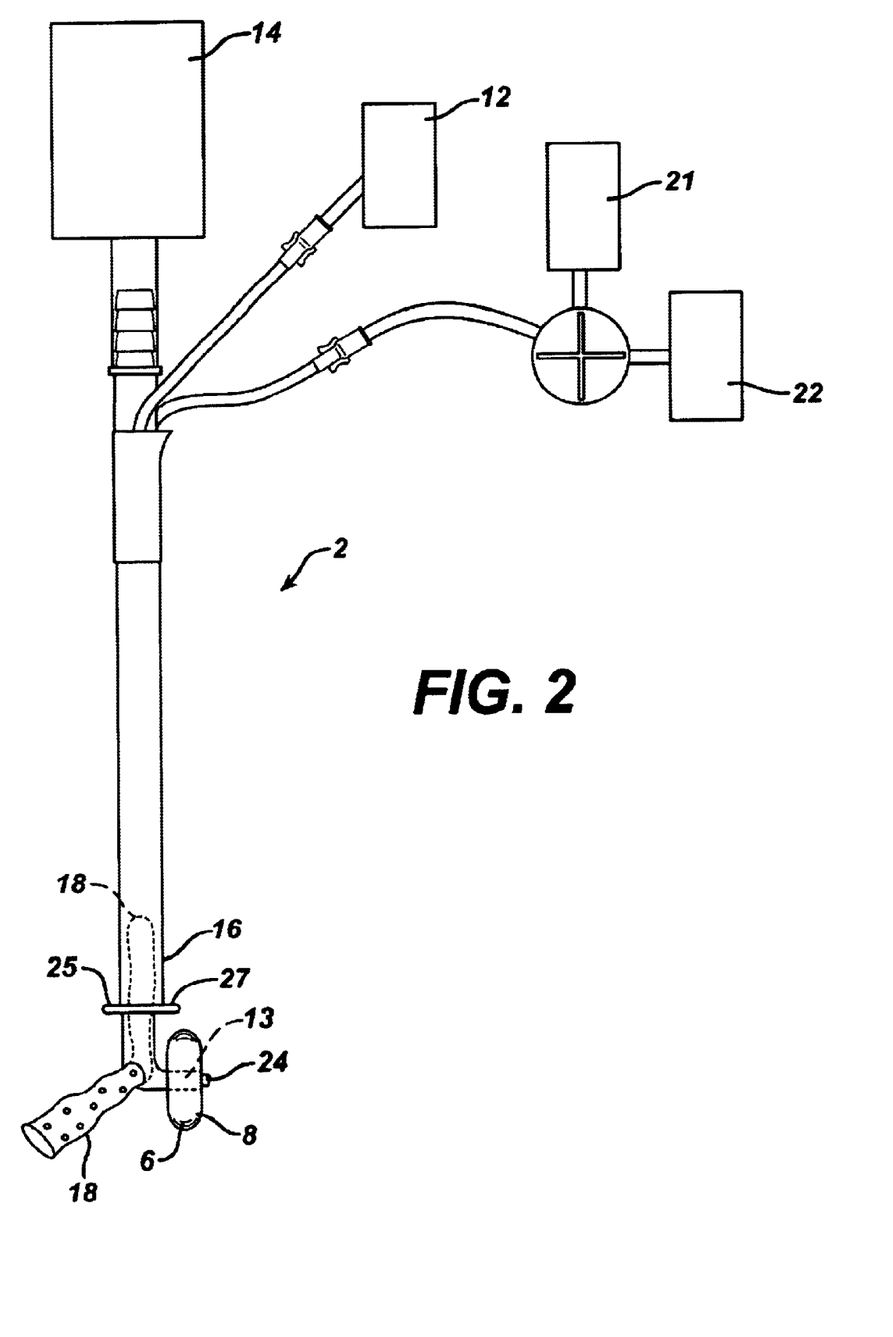
FIG. 2 shows the device of FIG. 1.
Figure 3:
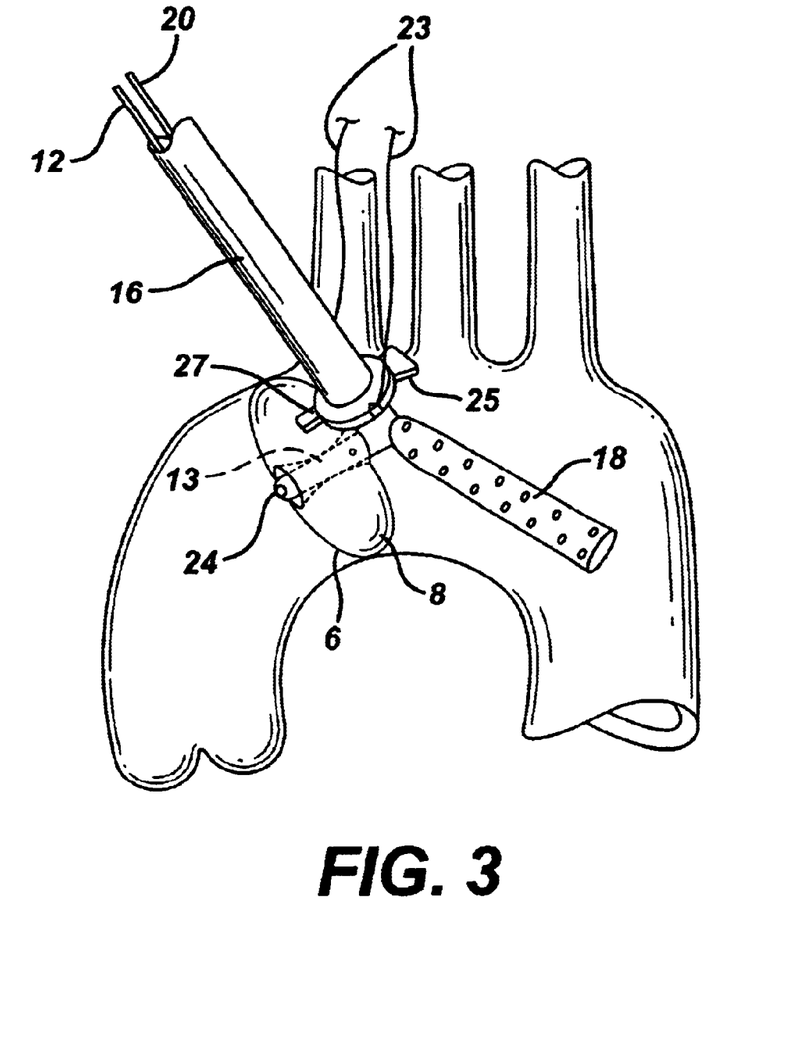
FIG. 3 shows the movable portion extending from the body of the device.

Referring to FIGS. 1–3, a device 2 for occluding the ascending aorta and delivering oxygenated blood to a patient is shown. The device 2 has a body 4 with an expandable member 6 mounted thereto. The body 4 may be made of any suitable material and may be reinforced by a reinforcing element such as a wire (not shown.) The expandable member 6 is preferably an inflatable balloon 8 coupled to an inflation lumen 10 and a source of inflation fluid 52 such as saline. The expandable member 6, may, of course, also be a mechanically actuated expandable member.

The device 2 has a blood flow lumen 12 extending through the body 4. The blood flow lumen 12 is coupled to a source of oxygenated blood 14. The source 14 may include a pump, oxygenator filter, and/or heat exchanger. The blood is delivered to the patient to maintain bypass support when the patient's heart is arrested. The blood flow lumen 12 has a relatively rigid, fixed portion 16 and a movable portion 18. The movable portion 18 may be made of any suitable material and is preferably a flexible tube made of a suitable material such as polyurethane or PTFE. The body has a tapered tip 13 with the expandable member 6 being preferably mounted to the tapered tip 13. The tapered tip 13 facilitates introduction of the device 2.

The movable portion 18 is preferably contained within the fixed portion 16 during introduction of the device 2 as shown in dotted line position 18. When the oxygenated blood is delivered through the blood flow lumen 12, the movable portion 18 preferably everts as shown in FIGS. 1 and 2 and extends outwardly from the body 4. The movable portion 18 may also be moved to the extended position with a manually operated pusher (not shown). The movable portion 18 provides a soft, atraumatic lumen for delivery of the oxygenated blood to the patient.

The device 2 may also include a lumen 20 coupled to a source of cardioplegic fluid 22 which is delivered to arrest the patient's heart. The source of cardioplegic fluid 22 may receive blood from the source of oxygenated blood 14 and mix the blood with the cardioplegic substance. The lumen 20 has an outlet 24 which is positioned on the opposite side of the expandable member 6 from the blood flow lumen 12. The lumen 20 may also be used to vent the ascending aorta with a vacuum source 21. Although the device 2 preferably includes the lumen 20, the lumen 20 is not necessary for practicing many aspects of the invention. A removable introducer (not shown) may be positioned through the body 4 to facilitate introduction of the device 2 into the ascending aorta. The tapered tip facilitates introduction of the device 2 and may be used to dilate the aorta during insertion.

A method of the present invention is now described in connection with the device 2 of FIGS. 1–3 although any other suitable device may be used. First, the surgeon gains access to the ascending aorta with any suitable technique including minimally invasive, less invasive or conventional open chest procedures. Sutures 23, typically a purse string suture, is placed in the desired location for introduction of the device 2 and the device 2 is introduced into the aorta with the sutures 23 providing hemostasis. The device 2 preferably has a flange 25 which lies against the surface of the aorta.

The flange 25 has an indicator 27 which is oriented in the desired direction which may help to align the angled tip of the device 2. The aorta may be incised with a conventional scalpel or the like. The device 2 is then introduced into the aorta. During introduction into the ascending aorta, the movable portion 18 of the blood flow lumen 12 is contained within the fixed portion 16 of the blood flow lumen 12.

Figure 4:
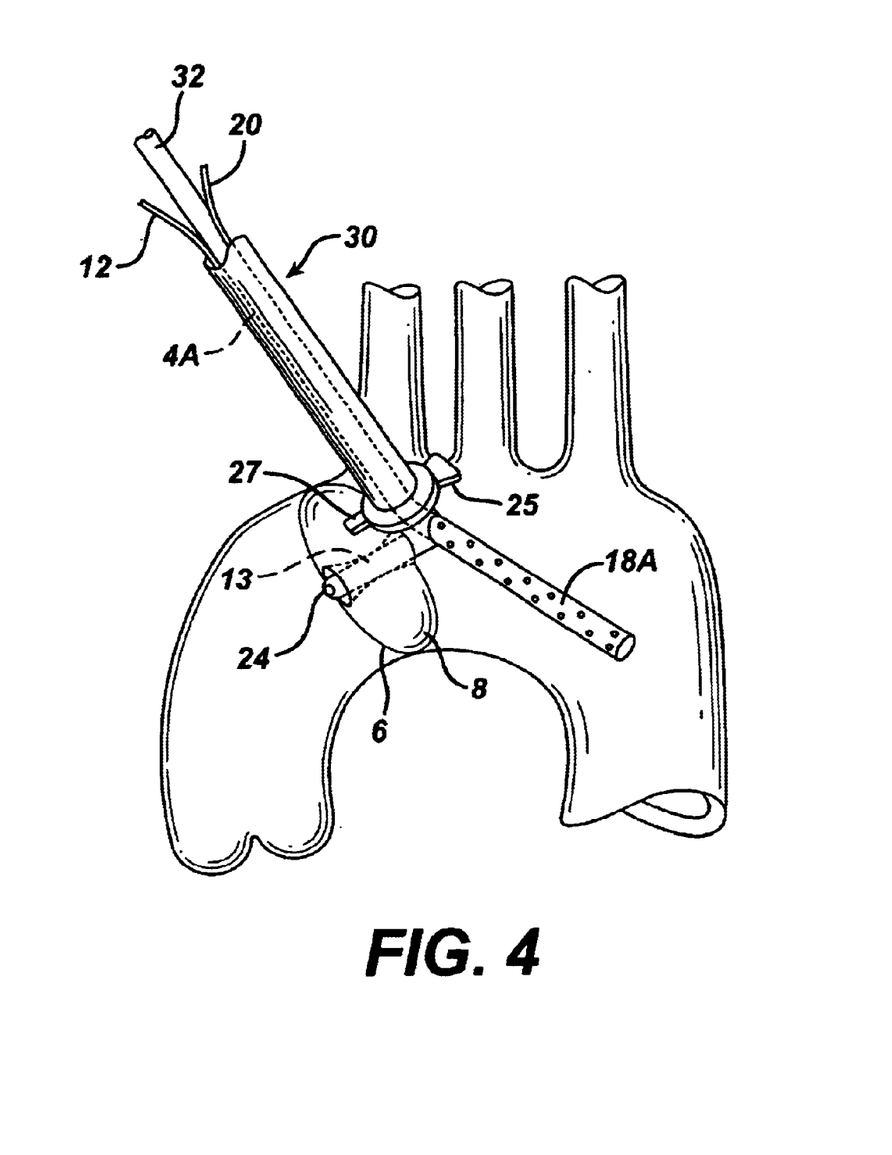
FIG. 4 shows another device which has a movable portion which is manually moved.

The blood flow lumen 12 is coupled to the source of oxygenated blood 14 and blood is then delivered to the patient at the appropriate time. When blood is delivered through the blood flow lumen 12, the movable portion 18 everts out of the fixed portion 16 as shown in FIGS. 3 and 4. The ascending aorta is occluded by expanding the expandable member 6 and the patient's heart is stopped by delivering cardioplegic fluid through the lumen 20. Cardioplegic fluid may be delivered with a separate needle in the conventional manner but is preferably delivered through the lumen 20 in the device 2.

Figure 5:
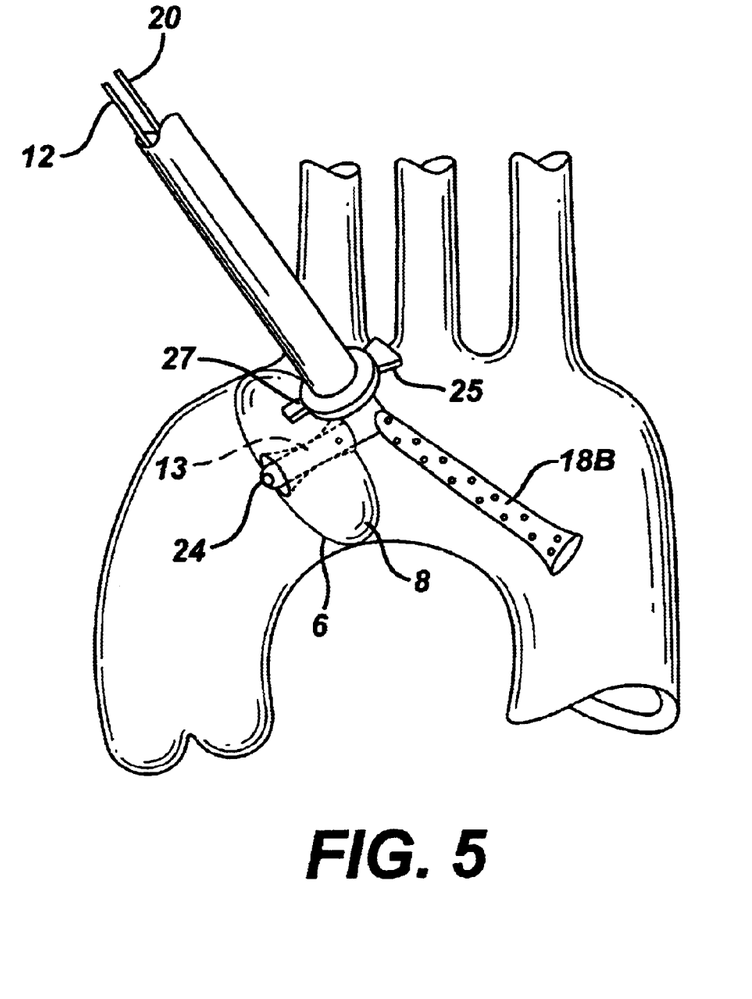
FIG. 5 shows a movable portion having a flared end.
Figure 6:
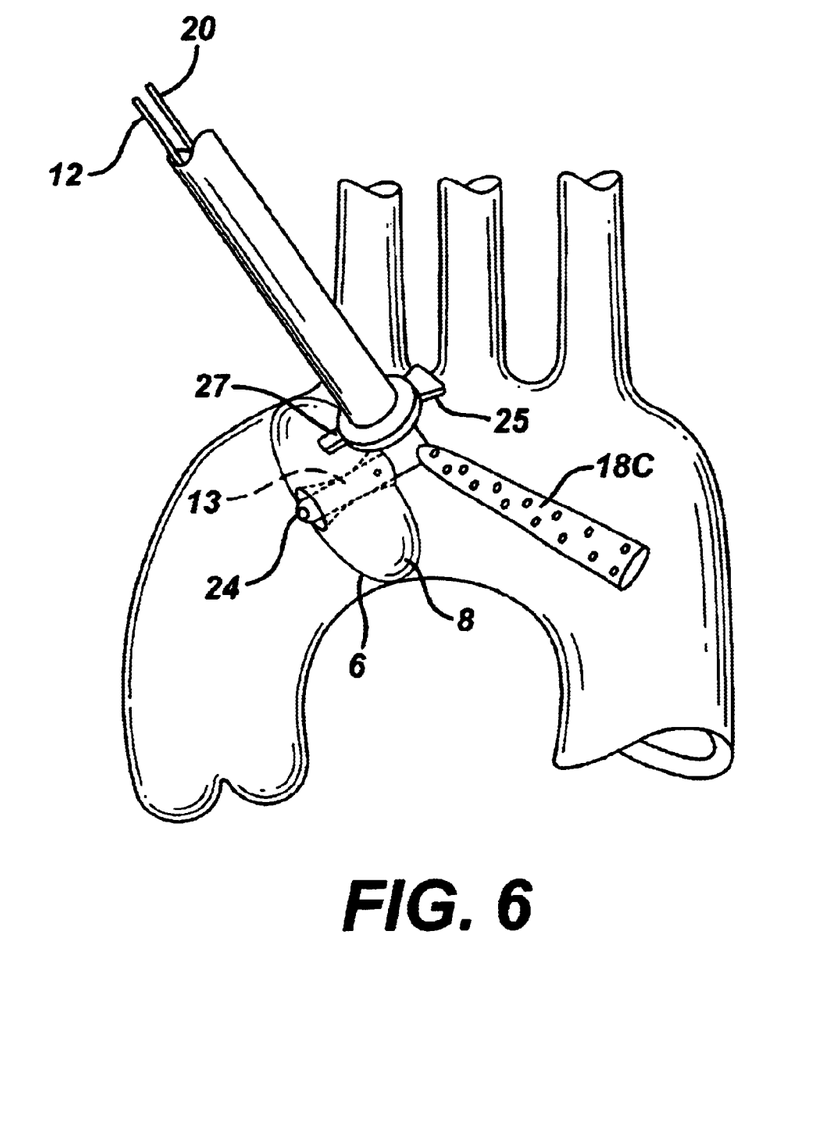
FIG. 6 shows the movable portion being tapered.

Referring to FIG. 4, another device 30 for occluding the ascending aorta and delivering oxygenated blood is shown wherein the same or similar reference numbers refer to the same or similar structure. The device 30 has the body 4A and a movable portion 18A which is manually movable. The movable portion 18A has a lumen 32 which is manually advanced and retracted to move the portion 18A. The lumen 32 is coupled to the source of oxygenated blood 14. The body 4A has the inflation lumen 10 for inflating the balloon 8 and the lumen 20 for delivering cardioplegic fluid and/or venting the aorta. Referring to FIG. 5, movable portion 18B may be flared at the end or a tapered movable portion 18C in the manner shown in FIG. 6.

Figure 7:
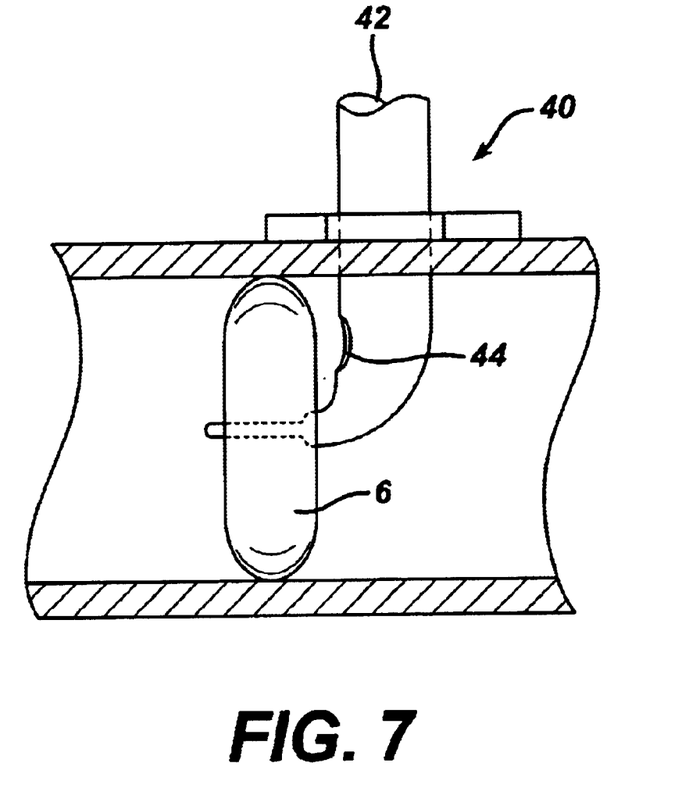
FIG. 7 shows still another device for occluding the ascending aorta and delivering oxygenated blood to the patient.

Referring to FIG. 7, still another device 40 for occluding the patient's ascending aorta and delivering oxygenated blood is shown wherein the same or similar reference numbers refer to the same or similar structure. The device 40 has a blood flow lumen 42 having an outlet 44 directed at the expandable member 6. In this way, the blood flow is dispersed by the expandable member 6, which is preferably the balloon 8, so that the blood flow is dispersed. The device 40 may also have the lumen 20 which is used in the manner described above.

The description of the invention is not intended to limit the invention and, furthermore, various features of the invention may be practiced independently of other features without departing from the scope of the invention.

What is claimed is:

1. A method of occluding a patient's ascending aorta and delivering oxygenated blood to the patient, comprising the steps of:

providing a device having a body, an expandable member and a blood flow lumen, the expandable member being movable from a collapsed shape to an expanded shape, the blood flow lumen having a movable portion which is movable relative to the body, the movable portion having an outlet;

introducing the device into the patient's aorta to position the expandable member in the ascending aorta;

moving the movable portion so that the movable portion moves to a position within the body to a position which extends outwardly from the body;

expanding the expandable member to occlude the ascending aorta; and delivering oxygenated blood to the patient through the blood flow lumen and out of the outlet of the movable portion.

2. The method of claim 1, wherein:

the providing step is carried out with the movable portion of the blood flow lumen being movable from a position contained entirely within the body to a position in which substantially the entire movable portion extends outwardly from the body.

3. The method of claim 1, wherein:

the moving step is carried out by everting the movable portion.

4. The method of claim 3, wherein:

the moving step is carried out with the movable portion being everted during the delivering step so that the flow of oxygenated blood evens the movable portion.

5. The method of claim 1, wherein:

the moving step is carried out manually by a user moving the movable portion so that the movable portion extends outwardly from the body.

6. The method of claim 1, wherein:

the providing step is carried out with the expandable member being an inflatable balloon.

7. The method of claim 1, wherein:

the providing step is carried out with the device having a cardioplege lumen, the cardioplege lumen being coupled to a source of cardioplegic fluid.

8. The method of claim 7, further comprising the step of:

delivering cardioplegic fluid through the cardioplege lumen to stop the patient's heart.

9. The method of claim 1, wherein:

the providing step is earned out with the movable portion comprising PTFE or polyurethane.

10. A device for occluding a patient's ascending aorta and delivering oxygenated blood to the patient, comprising:

a body;

an expandable member coupled to the body, the expandable member being movable from a collapsed shape to an expanded shape;

a blood flow lumen coupled to the body, the blood flow lumen configured to deliver blood and having a movable portion which is movable relative to the body, the movable portion being movable from a position contained within the body to an extended position in which the movable portion extends outwardly from the body.

11. The device of claim 10, wherein:

the moveable portion of the blood flow lumen is movable from a position contained entirely within the body to a position in which substantially the entire movable portion extends outwardly from the body.

12. The device of claim 10, wherein:

the movable portion everts when moving to the extended position.

13. The device of claim 10, wherein:

the movable portion is everted by a flow of oxygenated blood through the blood flow lumen.

14. The device of claim 10, wherein:

the moveable portion is manually movable by a user to the extended position.

15. The device of claim 10, wherein:

the expandable member is an inflatable balloon.

16. The device of claim 10, further comprising:

a cardioplege lumen extending through the body and being coupled to a source of cardioplegic fluid.

17. The device of claim 10, wherein:

the movable portion comprises PTFE or polyurethane.

18. The device of claim 10, wherein:
the body has a proximal portion and a distal portion, the distal portion having a smaller cross-sectional shape than the proximal portion;
the expandable member being mounted to the distal portion; and
the blood flow lumen terminates in the proximal portion and terminates before the expandable member.

19. The device of claim 10, wherein the blood flow lumen is configured to deliver blood into the aortic arch.

20. The device of claim 19, wherein the movable portion is configured to deliver blood in a direction away from the great arteries when the movable portion is in the extended position.

21. The device of claim 20, wherein the movable portion is configured to deliver blood downstream of the great arteries when the movable portion is in the extended position.

22. A device for occluding a patient's ascending aorta and delivering oxygenated blood to the patient, comprising:
a body having a blood flow lumen configured to deliver blood into the sortie arch;
an expandable member coupled to the body, the expandable member being movable from a collapsed shape to an expanded shape; and
a movable portion substantially disposed within the blood flow lumen, the movable portion configured to be movable between a first position where it is substantially disposed within the blood flow lumen and a second position where the movable portion extends outwardly from the body.

23. The device of claim 22, wherein the movable portion is configured to deliver blood in a direction away from the great arteries when the movable portion is in the second position.

24. The device of claim 22, wherein the movable portion is disposed substantially outside the blood flow lumen when the movable portion is in the second position.

25. The device of claim 22, wherein the movable portion is in fluid communication with the blood flow lumen when the movable portion is in the second position.

* * * * *